(12) United States Patent
Dale et al.

(10) Patent No.: US 11,903,934 B2
(45) Date of Patent: *Feb. 20, 2024

(54) RIFABUTIN TREATMENT METHODS, USES, AND COMPOSITIONS

(71) Applicant: BIOVERSYS AG, Basel (CH)

(72) Inventors: Glenn E. Dale, Basel (CH); Sergio Lociuro, Basel (CH); Marc Gitzinger, Laufenburg (CH); Stefano Biondi, Basel (CH); Marilyne Bourotte, Perenchies (FR)

(73) Assignee: BIOVERSYS AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 17/826,817

(22) Filed: May 27, 2022

(65) Prior Publication Data

US 2023/0066182 A1 Mar. 2, 2023

Related U.S. Application Data

(63) Continuation of application No. 16/983,667, filed on Aug. 3, 2020, now Pat. No. 11,344,537.

(60) Provisional application No. 62/977,659, filed on Feb. 17, 2020, provisional application No. 62/941,160, filed on Nov. 27, 2019, provisional application No. 62/902,019, filed on Sep. 18, 2019.

(51) Int. Cl.
| | | |
|---|---|---|
| *A61K 31/438* | (2006.01) |
| *A61K 9/00* | (2006.01) |
| *A61K 47/10* | (2017.01) |
| *A61K 47/12* | (2006.01) |
| *A61K 47/26* | (2006.01) |
| *A61K 47/22* | (2006.01) |
| *A61K 9/08* | (2006.01) |

(52) U.S. Cl.
CPC .......... *A61K 31/438* (2013.01); *A61K 9/0019* (2013.01); *A61K 9/0073* (2013.01); *A61K 9/08* (2013.01); *A61K 47/10* (2013.01); *A61K 47/12* (2013.01); *A61K 47/22* (2013.01); *A61K 47/26* (2013.01)

(58) Field of Classification Search
CPC .................................................. A61K 31/438
See application file for complete search history.

(56) References Cited

U.S. PATENT DOCUMENTS

| | | |
|---|---|---|
| 6,645,508 B1 | 11/2003 | Chen |
| 2019/0269806 A1 | 9/2019 | Timmins et al. |
| 2020/0222373 A1 | 7/2020 | Spellberg et al. |

FOREIGN PATENT DOCUMENTS

| | | |
|---|---|---|
| CN | 101362067 A | 2/2009 |
| CN | 102178604 A | 9/2011 |

(Continued)

OTHER PUBLICATIONS

"International Search Report and Written Opinion issued in International Application No. PCT/IB2020/000647, dated Nov. 2, 2020, 22 pages".

(Continued)

*Primary Examiner* — Benjamin J Packard
(74) *Attorney, Agent, or Firm* — Withers Bergman LLP; Thomas C. Meyers

(57) ABSTRACT

The invention provides formulations containing highly concentrated solutions of rifabutin and methods of making such formulations. The invention also provides methods of using such formulations to treat a bacterial infection in a subject.

10 Claims, 4 Drawing Sheets

(56) References Cited

FOREIGN PATENT DOCUMENTS

| EA | 016410 B1 | 4/2012 |
|---|---|---|
| WO | 2012039596 A2 | 3/2012 |
| WO | 2012106364 A1 | 8/2012 |
| WO | 2016178240 A1 | 11/2016 |

OTHER PUBLICATIONS

"International Search Report issued in International Application No. PCT/IB2020/000645, dated Nov. 27, 2020, 22 pages".

"Office Action issued in U.S. Appl. No. 16/983,689, dated Oct. 7, 2020, 8 pages".

Giannouli, "Molecular Epidemiology and Mechanisms of Rifampicin Resistance Inisolates from Italy", Journal of Antimicrobial Agents, vol. 36, No. 1, 2011, 58-63.

Horne, et al., The International Journal of Tuberculosis and Lung Disease, vol. 15, No. 11, Nov. 2011, 2011, 1485-1490.

Luna, "A Nurtient-Limited Screen Unmasks Rifabutin Hyperactivity for Extensively Drug-Resistant", Nature Publishing Group UK, London, vol. 5, No. 9, 2020, 1134-1143.

MacNair, "Overcoming mcr-1 Mediated Colistin Resistance with Colistin in Combination with Other Antibiotics", Nature Communication, vol. 9, No. 1, 8 pages, 2018.

Muller, Veterinary Medicine International, vol. Article IC 321797, 7 pages, 2010.

Nwugo, "Deciphering the Iron Response in Acinetobacter Baumannii: A Proteomics Approach", Journal of Proteomics, 74(1), 2011, 44-58.

Rajamani, "Robust Biofilm Assay for Quantification and High Throughput Screening Applications", Journal of Microbiological Methods, vol. 159:179-185, 2019.

Saisho, "Pharmacokinetics, Safety, and Tolerability of Cefiderocol, a Novel Siderophore Cephalosporin for Gram Negative Bacteria, in Healthy Subjects", Antimicrobial Agents and Chemotherapy, vol. 62, No. 3, 2 pages, 2018.

Sun, "Rapid antimicrobial Susceptibility Test for Identification of New Therapeutics and Drug Combinations Against Multidrug-Resistant Bacteria", Emerging Microbes and Infections, vol. 5, No. 1, 2016, 1-11.

Wong, "Clinical and Pathophysiological Overview of Acinetobacter Infections: A Century of Challenges", Clinical Microbiology Review, vol. 20, No. 1, 2017, 409-447.

Yu, "Novel Partners with Colistin to Increase its In Vivo Therapeutic Effectiveness and Prevent Occurence of Colistin Resistance in NDM- and MCR-co-producing *Escherichia coli* in a Murine Infection Model", Journal of Antimicrobial Chemotherapy, vol. 74, 2018, 87-95.

RIFABUTIN TREATMENT METHODS, USES, AND COMPOSITIONS

RELATED APPLICATIONS

This Application is a continuation of U.S. Nonprovisional patent application Ser. No. 16/983,667, filed Aug. 3, 2020, which claims the benefit of and priority to U.S. Provisional Patent Application Ser. Nos. 62/902,019, filed Sep. 18, 2019, 62/899,257, filed Sep. 12, 2019, 62/941,160, filed Nov. 27, 2019, and 62/977,659, filed Feb. 17, 2020, the content of each of which is incorporated herein in its entirety.

FIELD OF THE INVENTION

The invention generally related to formulations containing the antibiotic rifabutin, methods of the making such formulations, and methods of using such formulations in the treatment of bacterial infections.

BACKGROUND

Millions of people die each year from bacterial infections, and the numbers are increasing due to the spread of antibiotic-resistant bacterial strains. For example, according to official estimates, the annual number of deaths due to infections from antibiotic-resistant bacteria in the United States, European Union, and India alone is over 100,000, and some experts believe that official tallies are vast underestimates because the full impact of antibiotic resistance is still unknown. Unfortunately, the pipeline for development of new antibiotics in recent decades has slowed to a trickle, and many existing antibiotics are beset with problems that limit their effectiveness.

One existing antibiotic that has failed to reach its full therapeutic potential is rifabutin, also known as LM427 and Mycobutin®. Although rifabutin is active against a broad spectrum of bacteria, its poor water-solubility makes the antibiotic difficult to deliver at doses effective for treating infections other than those reported in the Mycobutin® label and to effectively prevent the development of resistance. Based on studies on rifabutin and related antibiotics of the same class, it is believed that high levels of free rifabutin are necessary both for microbial killing and to prevent development of resistance. Consequently, the therapeutic utility of rifabutin is hampered by technical problems, and millions of people continue to suffer from bacterial infections due to the lack of adequate treatment options.

SUMMARY

The invention provides pharmaceutical formulations that contain high concentrations of rifabutin. Preferred compositions of the invention comprise a rifabutin powder formulated in water, a solvent and an acid. The inventive combination allows dissolution of rifabutin at high concentration. The formulated solution may be diluted without restriction in order to render a composition suitable for a desired route of administration.

Formulations of the invention allow delivery of effective amounts of rifabutin by routes of administration that are not possible with prior rifabutin-containing compositions. For example, formulations of the invention enable rifabutin to be provided parenterally, including intravenously or by inhalation. In addition, formulations of the invention obviate the need to lyophilize rifabutin prior to reconstituting it for administration, a rather costly process.

In another aspect of the invention, rifabutin is prepared as a powder with a shelf-life equivalent to that of the rifabutin active pharmaceutical ingredient (API). As detailed below, rifabutin formulations of the invention preferably comprise rifabutin powder dissolved in an organic solvent.

According to the invention, highly concentrated rifabutin formulations are rapidly obtained from any rifabutin API and used as such or further diluted ad libitum with sterile water or pharmaceutically-acceptable solutions. Formulations of the invention are useful for treating a variety of conditions caused by or associated with bacterial infections, such as, but not limited to, bacteremia, meningitis, Ventilator-Associated Bacterial Pneumonia (VABP), Hospital-Acquired Bacterial Pneumonia (HABP) and Periprosthetic Joint Infections (PJI).

In one aspect, the invention provides non-oral formulations of rifabutin manufactured by preparing a solution in the presence of an acid suitable to promote dissolution of rifabutin. The solution preferably includes a solvent and water in a ratio appropriate for the intended use of the formulation.

A formulation of the invention is suitable for any non-oral route of administration. The formulation is suitable for parenteral, intravenous, intraarterial administration, or pulmonary delivery. The formulation is also suitable for administration by inhalation or by injection.

Formulations of the invention are reconstituted solutions that may need to be diluted prior to non-oral administration. A formulation of the invention includes solvent and water in a defined ratio. The ratio may be a v/v ratio. The solution may include the solvent and distilled water in a ratio of from about 9:1 to about 1:9, from about 9:1 to about 1:4, from about 9:1 to about 1:2, from about 9:1 to about 1:1, from about 4:1 to about 1:9, from about 4:1 to about 1:4, from about 4:1 to about 1:2, from about 4:1 to about 1:1, from about 2:1 to about 1:9, from about 2:1 to about 1:4, from about 2:1 to about 1:2, or from about 2:1 to about 1:1. The solution may include the solvent and distilled water in ratio of about 9:1, about 4:1, about 2:1, about 1:1, about 1:2, about 1:4, or about 1:9.

The solvent may be polyoxyethylene sorbitan monooleate (Tween 80), sorbitan monooleate polyoxyethylene sorbitan monolaurate (Tween 20), polyethylene glycol (PEG), propylene glycol, N-methyl-2-pyrrolidone (NMP), glycerin, ethanol, dimethylacetamide (DMA), diethylene glycol monoethyl ether (transcutol HP), or dimethyl isosorbide (DMI).

The acid may be hydrochloric, methanesulfonic, phosphoric, L-tartaric, D-glucuronic, L-malic, D-gluconic, L-lactic, acetic, or L-aspartic acid.

A reconstituted solution of the invention preferably contains about 250 mg/ml (1:1 solvent/water) or about 166.7 mg/ml. (1:2 solvent/water), however concentrations of the reconstituted solution may be as high as about 300 mg/ml. In certain embodiments, a more dilute solution is required and that is obtained by adding more water to the solvent. For example, rifabutin in a 1:4 solvent/water ratio will result in a solution of about 50 mg/ml. However, such a dilution will take additional time to dissolve rifabutin powder. Alternatively, rifabutin can be dissolved in a solvent and reconstituted solutions are then obtained without further modification. In general, for an IV solution, the desire is to keep the rifabutin/solvent ratio as low as possible. Appropriate ranges are provided herein.

Formulations of the invention are effective for treatment of a bacterial infection. The infection may include one or more of *A. baumannii, C. jejuni, C. trachomatis, H. ducreyi,*

H. influenzae, H. pylori, M. chelonae, M. kansasii, M. leprae, M. tuberculosis, Mycobacterium avium, Mycobacterium intracellulare, N. gonorrhoeae, N. meningitidis, staphylococci, streptococci (e.g., group A streptococci), and T. gondii or any other pathogen that is susceptible to rifabutin.

The amount of acid relative to rifabutin may be between 1 and 3 molar equivalents or between 1 and 2 molar equivalents. The amount of acid relative to rifabutin may be 1 molar equivalent.

The w/v ratio of rifabutin to solvent may be from about 4:1 to about 1:4, from about 2:1 to about 1:3, or from about 1:1 to about 1:2. The w/v ratio of rifabutin to solvent may be about 4:1, about 3:1, about 2:1, about 1:1, about 1:2, about 1:3, or about 1:4.

In another aspect, the invention provides methods of preparing a non-oral formulation of rifabutin by preparing a solution including a solvent and distilled water, adding an acid to the solution, and introducing this solution to rifabutin powder, causing the rifabutin to dissolve in the solution.

In another aspect, the invention provides methods of preparing a non-oral formulation of rifabutin by preparing a solution of rifabutin in solvent and a solution of the acid in water and then mixing the two solutions.

The formulation may have any of the properties described above in relation to formulations. The acid and solvent may be any of those described above. The water and solvent may be combined at any ratio described above.

Methods of the invention include diluting a formulated rifabutin solution without restriction in order to render a composition suitable for a desired route of administration into a pharmaceutically acceptable diluent such as, but not limited to, sterile water, sodium chloride (i.e., saline) solution, dextrose water, Ringer lactate solution.

The step of dissolving the rifabutin may include swirling, stirring, or agitation of the solution. The step of dissolving the rifabutin may be performed for a defined period. The step of dissolving the rifabutin may be performed for about 5 minutes, about 10 minutes, about 15 minutes, about 20 minutes, about 30 minutes, about 45 minutes, or about 60 minutes.

The rifabutin may be provided as a solid powder.

The rifabutin may be provided as a solution in solvent.

In another aspect, the invention provides methods of treating a bacterial infection in a subject by administering a therapeutically effective amount of a non-oral formulation of rifabutin.

The bacterial infection may include one or more of A. baumannii, C. jejuni, C. trachomatis, H. ducreyi, H. influenza, H. pylori, M. chelonae, M. kansasii, M. leprae, M tuberculosis Mycobacterium avium, Mycobacterium intracellulare, N. gonorrhoeae, N. meningitidis, staphylococci, streptococci (e.g., group A streptococci), and T. gondii or any other pathogen that is susceptible to rifabutin.

The formulation may have any of the properties described above in relation to formulations.

The formulation may be provided parenterally, intravenously, or by inhalation.

Aspects of the disclosure provide a use of rifabutin, an acid, a solvent, and a diluent for making a medicament for treating a bacterial infection.

In certain embodiments, the diluent is water.

In certain embodiments, the w/v ratio of rifabutin to solvent may be about 4:1, about 3:1, about 2:1, about 1:1, about 1:2, about 1:3, or about 1:4.

In certain embodiments, the w/v ratio of rifabutin to solvent is about 1:2.

In certain embodiments, the solvent is polyoxyethylene sorbitan monooleate (Tween 80), sorbitan monooleate polyoxyethylene sorbitan monolaurate (Tween 20), polyethylene glycol (PEG), propylene glycol, N-methyl-2-pyrrolidone (NMP), glycerin, ethanol, dimethylacetamide (DMA), diethylene glycol monoethyl ether (transcutol HP), or dimethyl isosorbide (DMI).

In certain embodiments, the solvent is DMI or transcutol HP.

In certain embodiments, the solvent and water are present in a ratio of from about 9:1 to about 1:9, from about 9:1 to about 1:4, from about 9:1 to about 1:2, from about 9:1 to about 1:1, from about 4:1 to about 1:9, from about 4:1 to about 1:4, from about 4:1 to about 1:2, from about 4:1 to about 1:1, from about 2:1 to about 1:9, from about 2:1 to about 1:4, from about 2:1 to about 1:2, or from about 2:1 to about 1:1.

In certain embodiments, the solvent and water are present in a ratio of from about 1:1 to about 1:2.

In certain embodiments, the acid is hydrochloric, methanesulfonic, phosphoric, L-tartaric, D-glucuronic, L-malic, D-gluconic, L-lactic, acetic, or L-aspartic acid.

In certain embodiments, the acid may be D-glucoronic acid.

In certain embodiments, the acid may be acetic acid.

In certain embodiments, the amount of acid relative to rifabutin is between 1 and 3 molar equivalents or between 1 and 2 molar equivalents.

In certain embodiments, the amount of acid relative to rifabutin may is 1 molar equivalent.

In certain embodiments, the rifabutin to acid molar ratio is about 1:1.

In certain embodiments, the w/v ratio of rifabutin to solvent may be from about 4:1 to about 1:4, from about 2:1 to about 1:3, or from about 1:1 to about 1:2.

In certain embodiments, the bacterial infection is A. baumannii, C. jejuni, C. trachomatis, H. ducreyi, H. influenza, H. pylori, M. chelonae, M. kansasii, M. leprae, M tuberculosis Mycobacterium avium, Mycobacterium intracellulare, N. gonorrhoeae, N. meningitidis, staphylococci, streptococci (e.g., group A streptococci), or T. gondii.

In another aspect, the invention provides formulations comprising rifabutin, an acid, water, and a solvent suitable to promote dissolution of the rifabutin.

The formulations may contain any ratio of rifabutin to solvent, any ratio of solvent to water, or any ratio of rifabutin to acid described above.

The formulations may contain any solvent or any acid described above.

The formulation may contain any concentration of rifabutin, such as about 250 mg/ml, about 200 mg/ml, about 150 mg/ml, about 100 mg/ml, about 50 mg/ml, about 20 mg/ml, about 10 mg/ml, about 5 mg/ml, about 2.5 mg/ml, about 1 mg/ml, at least about 250 mg/ml, at least about 200 mg/ml, at least about 150 mg/ml, at least about 100 mg/ml, at least about 50 mg/ml, at least about 20 mg/ml, at least about 10 mg/ml, at least about 5 mg/ml, at least about 2.5 mg/ml, at least about 1 mg/ml, from about 1 mg/ml to about 250 mg/ml, from about 2.5 mg/ml to about 250 mg/ml, from about 5 mg/ml to about 250 mg/ml, from about 10 mg/ml to about 250 mg/ml, from about 20 mg/ml to about 250 mg/ml, from about 50 mg/ml to about 250 mg/ml, from about 100 mg/ml to about 250 mg/ml, from about 1 mg/ml to about 200 mg/ml, from about 2.5 mg/ml to about 200 mg/ml, from about 5 mg/ml to about 200 mg/ml, from about 10 mg/ml to about 200 mg/ml, from about 20 mg/ml to about 200 mg/ml, from about 50 mg/ml to about 200 mg/ml, or from about 100 mg/ml to about 200 mg/ml.

DETAILED DESCRIPTION

Rifabutin and Challenges of Administering Rifabutin

Figure 1:
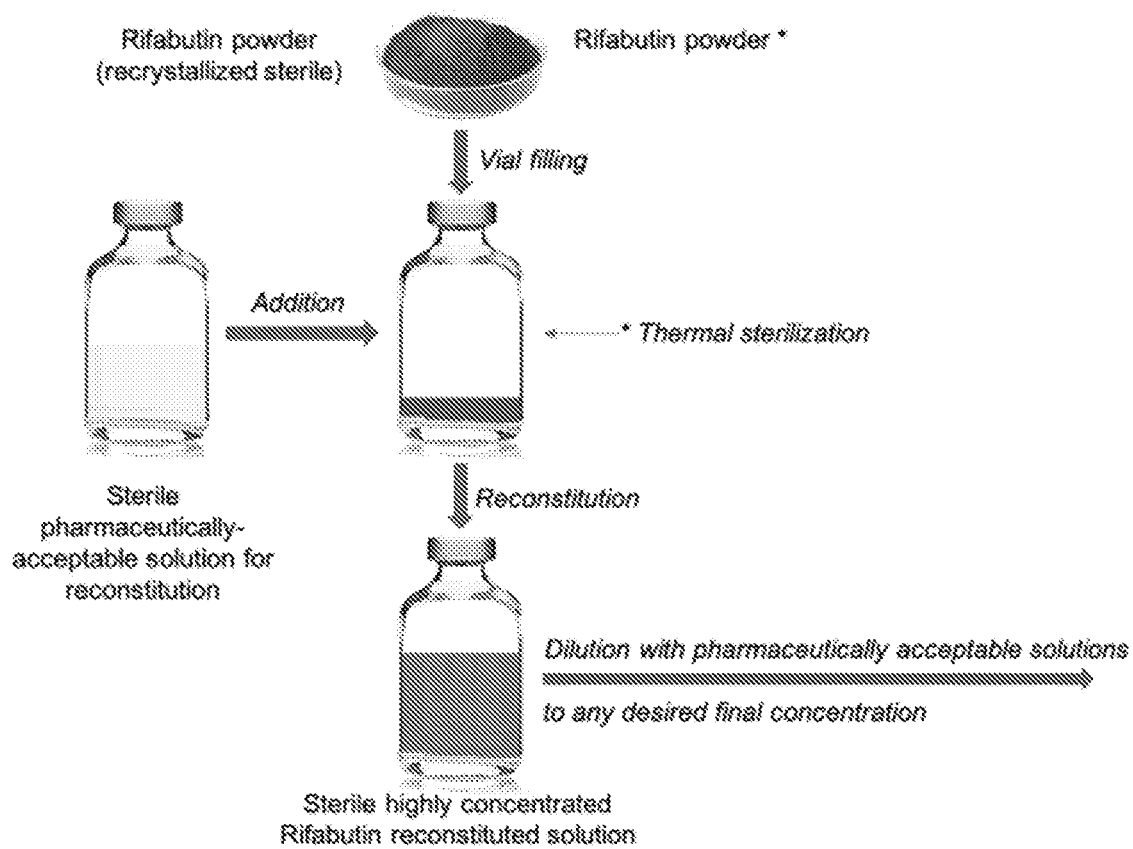
FIG. 1. is a schematic illustration of a method for preparing an injectable rifabutin solution or rifabutin for inhalation according to embodiments of the invention.

The invention provides compositions and methods for the preparation of solutions containing rifabutin suitable for parenteral or inhalatory administration. Importantly, the invention enables intravenous administration of rifabutin at high doses. The intravenous formulations of rifabutin permit delivery of the compound with much higher efficiency and efficacy than that can be achieved with prior oral rifabutin formulations. In particular the invention discloses the use of water/solvent mixtures in the presence of an acid as a pharmaceutically acceptable solution for reconstitution of rifabutin powder for a rapid preparation of a stable highly-concentrated reconstituted solution, which, in turn, can be diluted without restriction with additional water for injection or with pharmaceutically acceptable diluents in order to render a composition suitable for a desired route of administration.

Formulations of the invention are related to the requirement that high concentrations of rifabutin at the site of infection are optimal for reaching the appropriate Pharmacokinetics (PK) parameters, such as Areas Under the Curve (AUC) and $C_{max}$, which are needed for highest clinical efficacy and prevention of resistance in the treatment of bacterial infections against which rifabutin is active.

Rifabutin is a dark red-violet powder, has a molecular formula of $C_{46}H_{62}NO_{11}$, a molecular weight of 847.02 and the following structure:

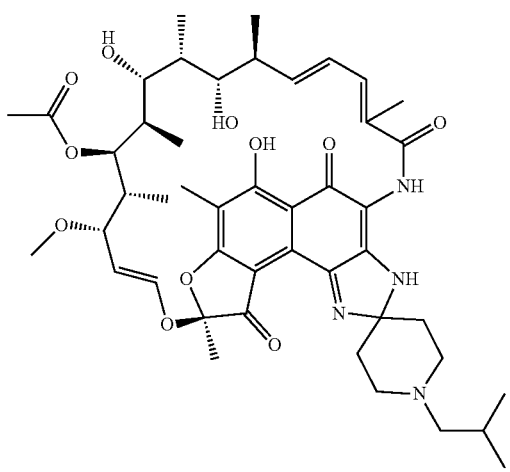 [SMILES: CO[C@H]1/C=C/O[C@@]2(C)Oc3c(C)c(O)c4c(c3C2=O)C2=NC3(CCN(CC(C)C)CC3)NC2=C(NC(=O)/C(C)=C/C=C/[C@H](C)[C@H](O)[C@@H](C)[C@@H](O)[C@@H](C)[C@H](OC(C)=O)[C@@H]1C)C4=O]

Rifabutin has a broad spectrum of antimicrobial activity. It is considerably more active than rifampin against MAC, *M. tuberculosis*, and *M. leprae*. It is also active against most atypical mycobacteria, including *M. kansasii*; *M. chelonae*, however, is relatively resistant. Rifabutin is also active against staphylococci, group A streptococci, *N. gonorrhoeae*, *N. meningitidis*, *H. influenza*, *H. ducreyi*, *C. jejuni*, *H. pylori*, *C. trachomatis*, *T. gondii* and *A. baumannii*.

In healthy adult volunteers a nominal therapeutic oral dose of 300 mg Rifabutin produces a mean $C_{max}$ of 0.375 mg/L which is attained at approximately 3 hours after oral administration (rifabutin product monograph). The PK of rifabutin is linear after single administration of 300, 450 and 600 mg PO to healthy volunteers with a $C_{max}$ in the range of 0.4 to 0.7 mg/L (rifabutin product mongraph). In a study in HIV-infected patients receiving the recommended daily dose of rifabutin (300 mg/day) the plasma concentrations at steady state were Cmax=0.59±0.33 mg/L and the AUC was 8.6±8.2 mg*h/L (Hafner et al, 1998). Since rifabutin is approximately 90% protein bound the free drug concentrations after oral administration are very low. In healthy adult volunteers at least 53% of the oral dose is absorbed whereas the absolute bioavailability assessed in HIV-positive patients in a multiple dose study was 20% on day 1 and 12% on day 28.

In closely related rifamycin molecules, such as rifampicin, microbial killing is linked to the area under the concentration-time curve-to-minimum-inhibitory-concentration (MIC) ratio (AUC/MIC) whereas the suppression of resistance was associated with the free peak concentration ($C_{max}$-to-MIC ratio ($C_{max}$/MIC) and not to the duration that the rifampin concentration was above MIC. Moreover, the post-antibiotic effect duration was also most closely related to the $C_{max}$/MIC ratio. Gumbo T, Louie A, Deziel M R, Liu W, Parsons L M, Salfinger M, Drusano G L. Concentration-dependent *Mycobacterium tuberculosis* killing and prevention of resistance by rifampin. Antimicrob Agents Chemother. 2007, 51(11):3781-8, the contents of which are incorporated herein by reference. Thus, to achieve a microbial killing and to prevent the emergence of resistance in the clinical arena high plasma and/or high local concentrations of rifabutin are required.

Emergence of resistance to multiple antimicrobial agents in pathogenic bacteria has become a significant public health threat as there are increasingly fewer, or even no effective antimicrobial agents available for infections caused by these bacteria. Gram-positive and Gram-negative bacteria are both affected by the emergence and rise of antimicrobial resistance.

The life-threatening infections caused by these pathogens are best treated in hospitals, using optimized dosing regimens that often involve parenteral administration and, in some cases, the additional use of nebulized antibiotics.

In this context, the intravenous (IV) and inhalation (IN) administration routes offer several advantages with respect to oral route in term of achieving a high cure rate:

a) with the oral route, only a variable fraction reaches the systemic circulation; the rest of the drug either passes the Gastro-Intestinal (GI) tract without being absorbed, or undergoes first pass effect, i.e. the metabolic transformation occurring in the liver leading to excretion of drug metabolic products through the bile or the kidneys.

b) with the oral route, the $C_{max}$ and the $t_{max}$, the time in which $C_{max}$ is achieved, are limited by the rate of absorption of the drug in the GI tract.

c) the rate of absorption in humans is very variable depending on the patient's age, presence of concomitant diseases and the infection diseases progression in the patient.

d) with the IV route, instead, the drug enters directly the bloodstream, $t_{max}$ is immediate and $C_{max}$ can be controlled by the drug concentration infused and the time in which it is infused. AUC, by definition, is the maximum that can be achieved with respect to any other administration route.

e) with the IN route, instead, the drug enters directly the lungs, and $C_{max}$ and distribution in the lungs can be controlled by the drug concentration and by the particle size produced by the specific nebulizer.

Both IV and IN routes allow rifabutin to reach high AUC/MIC and $C_{max}$/MIC, which are important for efficacy and protection from drug resistance development during treatment of infections of bacteria susceptible to the action of rifabutin. The IV route of administration allow optimization of these parameters in plasma and in any compartment where the drug can properly distribute and is therefore suitable for the treatment of infections such as e.g., bacteremia, meningitis, Periprosthetic Joint Infections (PJI) and severe lung infections such as Ventilator-Associated Bacterial Infections (VABP) and Hospital-Acquired Bacterial Infections (HABP); by IN route is instead possible to achieve high local concentrations in the lungs for the treatment any bacterial lung infections in all those cases in which a doctor would prefer to achieve very high drug lung concentrations without unnecessarily expose other body compartments to excessive drug levels. Alternatively, a doctor may decide to use rifabutin by the IN route in combination with an oral or a parenteral antibiotic.

The present invention comprises rifabutin formulations for intravenous (IV) administration. In another embodiment of the invention rifabutin is administered intravenously (IV) or by inhalation (IN).

Compositions and Formulations Containing Rifabutin

The invention provides compositions that contain formulations in which free base rifabutin is dissolved in water/solvent with acid.

The compositions thereof may be provided as pharmaceutically acceptable salts, such as nontoxic acid addition salts, which are salts of an amino group formed with inorganic acids such as but not limited to hydrochloric acid, hydrobromic acid, phosphoric acid, sulfuric acid and perchloric acid or with organic acids such as, but not limited to, acetic acid, maleic acid, tartaric acid, citric acid, succinic acid, methansulfonic acid, glucuronic acid, malic acid, gluconic acid, lactic acid, aspartic acid, or malonic acid.

In some embodiments, pharmaceutically acceptable salts include, but are not limited to, adipate, alginate, ascorbate, aspartate, benzenesulfonate, benzoate, bisulfate, borate, butyrate, camphorate, camphor sulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Preferably, hydrochloric, methanesulfonic, phosphoric, L-tartaric, D-glucuronic, L-malic, D-gluconic, L-lactic, acetic or L-aspartic acids may be used. Most preferably, acetic acid, L-lactic acid, D-gluconic acid or D-glucuronic acid is used.

The pharmaceutical composition may be administered by injection, infusion, implantation (intravenous, intramuscular, subcutaneous, or the like) or by inhalation in dosage forms, formulations, or via suitable delivery devices or implants containing conventional, non-toxic pharmaceutically acceptable carriers, solvents, diluents, and adjuvants. The formulation and preparation of such compositions are well known to those skilled in the art of pharmaceutical formulation.

Compositions of the invention for parenteral use may be provided in unit dosage forms (e.g., in single-dose ampoules and vials), in vials containing several doses and in which a suitable preservative may be added (see below), in prefilled syringes, or in prefilled IV bags. The pharmaceutical compositions described herein may be in the form suitable for sterile injection. As shown in FIG. 1, to prepare such a composition, to rifabutin in powder form, a solution of water in solvent with acid is added to promote dissolution. Alternatively, such composition can be prepared by preparing rifabutin in solvent and mixing it with a solution of water containing the acid.

As such, the invention provides methods of preparing an intravenous formulation of rifabutin. The method may include preparing a solution containing a solvent and distilled water. Preferably, the solution is in a 1:1 ratio or a 1:2 ratio. The solvent may be any solvent, but preferably is DMI or trascutol HP. An acid may be added to the solution. The acid may be suitable to promote dissolution of rifabutin. The acid may be any acid, but preferably acetic acid or D-glucuronic acid. The solution containing the acid may be added to the rifabutin powder. Thus, the acid causes the rifabutin to dissolve into the aqueous solution.

The rifabutin solution may be added to a pharmaceutically acceptable diluent. The diluent may be 0.9% saline.

For example, to prepare a solution of 20 mg/ml rifabutin in 4% DMI, first a 1:1 solution of dimethyl isosorbide (DMI) in distilled water is prepared. 0.169 ml of glacial acetic acid may then be added to 9.831 ml of the 1:1 DMI/water solution, forming a reconstitution solvent (RS). Then, 1 ml of RS is added to 250 mg of rifabutin to make a solution at 250 mg/ml. This RS-rifabutin solution is stirred or shaken until the rifabutin dissolves forming a dark deep red solution. Complete dissolution should occur in about 15-20 minutes. The concentrated solution is then diluted with 11.5 ml of water to make a final solution of rifabutin at 20 mg/ml in 4% DMI. The pH of the final solution is between 5 and 6.

In another example to prepare an intravenous solution of 2.5 mg/ml rifabutin in 0.5% DMI/0.9% sodium chloride solution, first a 1:1 solution of dimethyl isosorbide in distilled water is prepared. 0.169 ml of glacial acetic acid may then be added to 9.831 ml of the 1:1 DMI/water solution forming the RS. Then, 1 ml of RS is added to 250 mg of rifabutin to make a solution at 250 mg/ml. This RS-rifabutin solution is stirred or shaken until the rifabutin is completely dissolved (about 15-20 minutes). The concentrated solution is then diluted with 99 ml of 0.9% saline for injection to make a final solution of rifabutin at 2.5 mg/ml in 0.5% DMI in 0.9% saline, with a pH between 5.0 and 6.0.

In another example to prepare an intravenous solution of 5 mg/ml rifabutin in 1% transcutol HP/0.9% sodium chloride solution, first a 1:2 solution of trancutol HP in distilled water is prepared. 0.169 ml of glacial acetic acid may then be added to 14.831 ml of the 1:2 transcutol HP/water solution forming the RS. Then, 1.5 ml of RS is added to 250 mg of rifabutin to make a solution at 166.7 mg/ml. This RS-rifabutin solution is stirred or shaken until the rifabutin is completely dissolved (about 15-20 minutes). The concentrated solution is then diluted with 48.5 ml of 0.9% saline for injection to make a final solution of rifabutin at 5 mg/ml in 1% transcutol HP in 0.9% saline, with a pH between 5.0 and 6.0.

In another example, an intravenous solution of 40 mg/ml rifabutin in 8% DMI/0.9% sodium chloride solution is prepared using a solution of 250 mg of rifabutin in 0.5 ml of DMI, to which 0.5 ml of a solution of 114.6 mg/ml of D-glucuronic acid in distilled water is added. After 5 minutes swirling, the resulting RS-rifabutin solution at 250 mg/ml is diluted with 5.25 ml of 0.9% saline for injection to make a final solution of rifabutin at 40 mg/ml in 8% DMI in 0.9% saline, with a pH between 5.0 and 6.0.

Depending upon the needs of the patient, and the clinical conditions, administration of the composition by IV administration may be favored over oral administration because it allows for rapid introduction of the antibiotic into systemic circulation, provides complete bioavailability, allows to better control the pharmacokinetic parameters that are driving the pharmacological efficacy, and avoids issues of stability in the gastrointestinal tract and absorption.

The typical dosage of rifabutin is that able to reach plasma or local levels in which rifabutin $C_{max}$ is >2 mg/L but <50 mg/L and AUC is 10 mg*h/L<200 mg*h/L.

The rifabutin solution may be further diluted with a pharmaceutically acceptable diluents. For example, a 20 mg/mL IV solution of rifabutin may be further diluted with 0.9% saline to obtain a lower concentration of rifabutin for delivery of a less concentrated solution to a subject. Filtration may also be required for IV formulations of rifabutin disclosed herein. If needed, filtration can be performed both on the concentrated or on the final rifabutin solution.

Formulations of the invention may be for any parenteral administration. For example, the composition may be formulated for injection or infusion. The injection or infusion may be subcutaneous or intravenous. Preferably, the composition is formulated for intravenous administration. Preferably, the composition is formulated for intravenous or inhalatory administration. Accordingly, formulations of the invention may also include a pharmaceutically acceptable diluent. The pharmaceutically acceptable diluent may be in a concentration sufficient to deliver a therapeutically effective amount of rifabutin in IV formulation to a patient suffering from an infection. The pharmaceutically acceptable diluent may be saline or sterile water. Preferably, the diluent is 0.9% saline. The solution may be administered with a therapeutically effective amount of rifabutin to treat a patient suffering from an infection.

It should be noted that the various formulations of the invention described herein may be used with any of the methods of the invention, and thus the methods are not limited to any singular formulation.

Methods of Preparing Formulations Containing Rifabutin

The invention provides methods for preparing formulations of rifabutin.

FIG. 1. is a schematic representation illustrating a method for preparing an injectable rifabutin solution or rifabutin for inhalation according to embodiments of the invention. An intravenous rifabutin formulation may be manufactured by a process including preparing a sterile pharmaceutically acceptable solution for reconstitution comprising a solvent and distilled water in a 1:1 ratio in the presence of an acid suitable to promote dissolution of rifabutin. Rifabutin may be present in a solid form or a powder form that is soluble in a liquid medium. Rifabutin may be dissolved in an aqueous solution of a solvent and distilled water. Rifabutin may be soluble in an aqueous solution of 50% solvent (i.e., 1:1 solvent-distilled water) in the presence of an acid.

Rifabutin is soluble in an aqueous solution of 33.3% solvent (i.e., 1:2 solvent-distilled water) in the presence of an acid.

The formulation may be suitable for any non-oral route of administration. The formulation may be suitable for parenteral, intravenous, intraarterial administration. The formulation may be suitable for administration by inhalation.

The formulation may be a reconstituted solution that needs to be diluted prior to non-oral administration. The formulation may be a reconstituted solution suitable for non-oral administration.

The solution may include mixing the solvent and distilled water in a defined ratio. The ratio may be a v/v ratio. The solution may include the solvent and distilled water in a ratio of from about 9:1 to about 1:9, from about 9:1 to about 1:4, from about 9:1 to about 1:2, from about 9:1 to about 1:1, from about 4:1 to about 1:9, from about 4:1 to about 1:4, from about 4:1 to about 1:2, from about 4:1 to about 1:1, from about 2:1 to about 1:9, from about 2:1 to about 1:4, from about 2:1 to about 1:2, or from about 2:1 to about 1:1. The solution may include the solvent and distilled water in ratio of about 9:1, about 4:1, about 2:1, about 1:1, about 1:2, about 1:4, or about 1:9.

The solvent may be polyoxyethylene sorbitan monooleate (Tween 80), sorbitan monooleate polyoxyethylene sorbitan monolaurate (Tween 20), polyethylene glycol (PEG), propylene glycol, N-methyl-2-pyrrolidone (NMP), glycerin, ethanol, dimethylacetamide (DMA), diethylene glycol monoethyl ether (transcutol HP), or dimethyl isosorbide (DMI).

The acid may be hydrochloric, methanesulfonic, phosphoric, L-tartaric, D-glucuronic, L-malic, D-gluconic, L-lactic, acetic, or L-aspartic acid.

The formulation may include diluting the rifabutin-containing solution into a diluent. The diluent may be sterile water, sodium chloride (i.e., saline) solution, dextrose water, or Ringer lactate solution. The sodium chloride solution may be a 0.9% sodium chloride solution. The dextrose solution may be a 5% dextrose solution or a 10% dextrose solution.

The obtained solutions may require further dilution in a pharmaceutically acceptable solvent such as including but not limited to, sterile water, mannitol, such as 3-5% mannitol, 3% mannitol, 4% mannitol, 4.3% mannitol, and 5% mannitol, phosphate, acetate, additional tartrate, saline, such as physiological saline (0.9%), ½ physiological saline (0.45%), and 0.5% saline, and the like. For intravenous formulations, physiological saline (0.9%) is a preferred diluent or carrier.

Rifabutin may be reconstituted in a solution containing an acid in a quantity comprised between 1 and 3 molar equivalents in a solvent and water mixture in ratios v/v of from about 9:1 to about 1:9. The rifabutin to solvent ratio in w/v may be from 4:1 to 1:4. The dissolution times for obtaining the formulations may be less than 60 minutes. In particular the amount of acid may be 1 molar equivalent, the acid may be acetic acid or D-glucuronic acid, the solvent may be DMI or transcutol HP mixed with water in a 1:1 or 1:2 v/v ratio, the rifabutin to solvent ratio w/v may be 1:2 and the dissolution time is less than 20 minutes.

The formulation (i.e., the reconstituted rifabutin solution) may be used as such or may be made by diluting it into a defined volume of diluent. The volume of diluent may be expressed relative to the volume of reconstituted solution. The volume of diluent may be from about 1.0 to about 2.0 volumes, from about 1.25 to about 2.25 volumes, from about 1.5 to about 2.5 volumes, from about 1.75 to about 2.75 volumes, from about 2.0 to about 3.0 volumes, from about 1.80 to about 2.10 volumes, from about 1.90 to about 2.05 volumes, or from about 1.95 to about 2.0 volumes of the reconstituted rifabutin solution. The reconstituted rifabutin solution may be added to from about 20.5 to about 30 volumes, from about 21 to about 29 volumes, from about 22 to about 28 volumes, from about 23 to about 27 volumes, from about 23 to about 26 volumes, from about 23 to about 25 volumes, from about 23 to about 24 volumes, from about 22.5 to about 23.5 volumes, or from about 23.0 to about 23.5 volumes of 0.9% saline for injection. Accordingly, one volume of diluent leads to a final solution of about 125 mg/ml, 4 volumes leads to a final solution of about 50 mg/ml, 9 volumes leads to a final solution of about 25 mg/ml, 24 volumes leads to a final solution of about 10 mg/ml, and 99 volumes leads to a final solution of about 2.5 mg/ml. The skilled artisan understands how to make a solution with any desired final concentration.

The formulation may contain rifabutin at any suitable concentration, such as those described above.

The formulation may contain DMI at any concentration, such as those deriving from the dilutions described above.

The formulation may contain transcutol HP at any concentration, such as those deriving from the dilutions described.

The amount of acid relative to rifabutin may be between 1 and 3 molar equivalents or between 1 and 2 molar equivalents. The amount of acid relative to rifabutin may be 1 molar equivalent.

The w/v ratio of rifabutin to solvent may be from about 4:1 to about 1:4, from about 2:1 to about 1:3, or from about 1:1 to about 1:2. The w/v ratio of rifabutin to solvent may be about 4:1, about 3:1, about 2:1, about 1:1, about 1:2, about 1:3, or about 1:4.

The method may include dissolving the rifabutin by swirling, stirring, or agitation of the solution. The dissolving step may be performed for a defined period. The dissolving step may be performed for about 5 minutes, about 10 minutes, about 15 minutes, about 20 minutes, about 30 minutes, about 45 minutes, or about 60 minutes.

Methods of Treating Bacterial Infections

The invention provides methods of treating a bacterial infection. The methods include administering a liquid formulation of rifabutin to a subject with a bacterial infection. The liquid formulation may include rifabutin, a solvent and an acid.

The formulation may be provided by intravenous, intraarterial, or pulmonary administration. The formulation may be provided by inhalation or by injection.

The liquid formulation may be a solution of rifabutin and a diluent to be administered intravenously to a subject with a bacterial infection. The formulation for IV administration may include a pharmaceutically acceptable solvent. The method may include administering an IV formulation of any formulation of rifabutin described herein to a subject suffering from a bacterial infection.

The IV formulation containing rifabutin may be administered with another antibiotic or therapeutic. Sequential administration or alternating administration may include providing IV formulation containing rifabutin exclusively for a period of time and providing the other therapeutic exclusively for a period of time. Sequential administration may include a period of overlap in which the subject is provided both the IV formulation containing rifabutin and the formulation containing the other therapeutic. The periods of exclusivity and periods of overlap may independently be 1 hour, 2 hours, 3 hours, 4 hours, 5 hours, 6 hours, 1 day, 2 days, 3 days, 4 days, 5 days, 6 days, 1 week, 2 weeks, 3 weeks, 4 weeks, 2 months, 3 months, 4 months, 5 months, 6 months, 8 months, 10 months, 12 months, 18 months, or 24 months. Alternatively, the pharmaceutical formulations of the invention, or the soluble components within the formulation, may contain rifabutin and another therapeutic.

Without wishing to be bound to theory, any formulations of the invention may be used in any of the methods of the invention.

In another aspect of the invention, methods include treating a bacterial infection in a subject. The method may include administering a therapeutically effective amount of a formulation comprising rifabutin or a salt thereof. The rifabutin formulation may be formulated for intravenous administration. The intravenous formulation is manufactured by a process comprising preparing a solution of a solvent and distilled water in a 1:1 ratio in the presence of an acid suitable to promote dissolution of said rifabutin. Preferably, the solvent is DMI. Preferably, the solvent is transcutol HP. Preferably the intravenous formulation is approximately 2.5 mg/mL rifabutin in 0.5% DMI and 0.9% sodium chloride solution.

In another embodiment, the method may include providing a subject suffering from a bacterial infection a combination therapy of an IV formulation of rifabutin or a salt thereof and another therapeutic. The IV formulation may include a pharmaceutically acceptable solvent. The therapeutic may be in a formulation for IV administration.

The IV formulation containing rifabutin and the formulation containing another therapeutic may be provided or administered simultaneously, sequentially in either order, or in an alternating manner. Sequential administration or alternating administration may include providing IV formulation containing rifabutin exclusively for a period of time and providing the formulation containing the other therapeutic exclusively for a period of time. Sequential administration may include a period of overlap in which the subject is provided both the IV formulation containing rifabutin and the formulation containing the other therapeutic. The periods of exclusivity and periods of overlap may independently be 1 hour, 2 hours, 3 hours, 4 hours, 5 hours, 6 hours, 1 day, 2 days, 3 days, 4 days, 5 days, 6 days, 1 week, 2 weeks, 3 weeks, 4 weeks, 2 months, 3 months, 4 months, 5 months, 6 months, 8 months, 10 months, 12 months, 18 months, or 24 months.

In another embodiment rifabutin is filled into glass vials and sterilized using one of the procedures used for terminal sterilization. Such procedures are well known to those skilled in the art and may be performed using gamma radiation or thermal sterilization.

A 50:50 sterile solution of water for injection and a solvent containing approximately 1 molar equivalent of an acid is then added to sterile rifabutin to form the concentrated reconstituted solution.

In another embodiment the reconstituted rifabutin formulation is filtered sterile.

In another embodiment the diluted rifabutin formulation is filtered sterile.

EXAMPLES

Example 1

Preliminary assessment of solubility in solvents: To determine if pharmaceutical acceptable solvents could dissolve rifabutin powder and at which concentrations, an adequate volume of solvent sufficient to achieve a maximum target solubility of 300 mg/ml was added to small aliquots of rifabutin powder. After 24 h stirring at room temperature, samples were centrifuged, and the supernatant analyzed by HPLC. The rifabutin chromatographic peak area was compared against a titration curve. Results of this preliminary screening are reported in Table 1.

TABLE 1

Solubility results in formulation vehicles

| Solvent/solution | Solubility (mg/ml) at 24 h |
|---|---|
| Polyethylene glycol 400 (PEG400) | ≥110 |
| Propylene glycol | ≥92 |
| N-Methyl-2-pyrrolidone (NMP) | ≥190 |
| Dimethylacetamide (DMA) | ≥204 |
| Transcutol HP | ≥206 |
| Glycerol | 0.4 |
| Tween 80 (1% w/w in water) | 1.3 |
| Povidone K12 (5% w/w in water) | 0.5 |
| Dimethyl isosorbide (DMI) | ≥245 |
| Saline 0.9% | 0.3 |
| Acetate buffer pH 4 (USP) | 11.3 |
| Phosphate buffer pH 6 (USP) | 0.3 |
| Phosphate buffer pH 8 (USP) | 0.2 |
| Borate buffer pH 10 (USP) | 1.9 |
| Ethanol (literature data) | 30 |

The "thermodynamic" solubility screen showed dimethyl isosorbide (DMI) as the best solvent. Although interesting, solubility data at 24 h are irrelevant in a reconstitution process of an antibiotic powder since a solvent for reconstitution must be able to dissolve the antibiotic in a few minutes, a time that is practical for an operator to prepare rifabutin for injection or for inhalation.

Dissolution of rifabutin in DMI at concentrations of >250 mg/ml was possible, but proven to be longer than plausibly acceptable. In addition, dilution of the DMI rifabutin solution with pharmaceutically acceptable solutions such as saline was impossible since the DMI-rifabutin solution separated from the aqueous solution.

Unexpectedly, addition of acid to a DMI/water solution allowed a rapid dissolution of rifabutin powder and, the highly concentrated reconstituted rifabutin solution could be diluted ad libitum with water or 0.9% saline without any rifabutin precipitation.

Example 2

Small scale solubility screen of solvents and acids: an amount of rifabutin powder comprised between 100 and 200 mg were weighed into 1.8 ml glass vials. Examples of solutions for reconstitution were prepared by mixing different solvents and water containing different acids in the amounts as specified in Table 2. The solutions were stirred at RT for 15 minutes using a magnetic stirring bar and were briefly vortexed. The samples were filtrated using centrifugal filters (0.2 μm PTFE filter), and the concentration the reconstituted solutions was determined by HPLC analysis. The rifabutin chromatographic peak area was compared against a titration curve and results are reported in Table 2.

TABLE 2

Small scale solubility screen

| Example No. | Solvent | Acid | RBT/solvent ratio (w/v) | RBT/acid ratio (mole/mole) | Solvent/water ratio (v/v) | Time to dissolution (min) | Notes | Approx. conc. (mg/ml) |
|---|---|---|---|---|---|---|---|---|
| 1 | DMI | — | 1:2 | — | 1:1 | ≥30 | not dissol. | 86 |
| 2 | DMI | HCl | 1:2 | 1:1 | 1:1 | ca. 20 | dissolved | 290 |
| 3 | DMI | Methanesulfonic | 1:2 | 1:1 | 1:1 | ca. 20 | dissolved | 280 |
| 4 | DMI | Phosphoric | 1:2 | 1:1 | 1:1 | ca. 20 | dissolved | 300 |
| 5 | DMI | L-tartaric | 1:2 | 1:1 | 1:1 | ca. 20 | dissolved | 240 |
| 6 | DMI | D-glucuronic | 1:2 | 1:1 | 1:1 | ca. 20 | dissolved | 300 |
| 7 | DMI | L-malic | 1:2 | 1:1 | 1:1 | ca. 20 | dissolved | 300 |
| 8 | DMI | D-gluconic | 1:2 | 1:1 | 1:1 | ca. 20 | dissolved | 300 |
| 9 | DMI | L-lactic | 1:2 | 1:1 | 1:1 | ca. 20 | dissolved | 260 |
| 10 | DMI | acetic | 1:2 | 1:1 | 1:1 | ca. 20 | dissolved | 290 |
| 11 | DMI | aspartic | 1:2 | 1:1 | 1:1 | ≥30 | not dissol. | 40 |
| 12 | DMA | D-glucuronic | 1:2 | 1:1 | 1:1 | ca. 20 | dissolved | ≥250 |
| 13 | DMA | acetic | 1:2 | 1:1 | 1:1 | ca. 20 | dissolved | ≥250 |
| 14 | PEG400 | — | 1:2 | — | 1:1 | ≥30 | not dissol. | not done |
| 15 | PEG400 | D-glucuronic | 1:2 | 1:1 | 1:1 | ≥30 | not dissol. | not done |
| 16 | PEG400 | acetic | 1:2 | 1:1 | 1:1 | ≥30 | not dissol. | not done |
| 17 | Transcutol | D-glucuronic | 1:2 | 1:1 | 1:2 | ca. 15 | dissolved | 130 |
| 18 | Transcutol | acetic | 1:2 | 1:1 | 1:2 | ca. 15 | dissolved | — |
| 19 | DMI | D-glucuronic | 1:2 | 1:1 | 1:2 | ca. 15 | dissolved | 150 |
| 20 | DMI | acetic | 1:2 | 1:1 | 1:2 | ca. 15 | dissolved | 160 |

TABLE 3

Solubility of rifabutin reconstituted solutions at t = 0 and t = 24 h

| Example No. | Solvent/water mix | Acid | Solubility (mg/ml) T0 | Solubility (mg/ml) T 24 h RT | Solubility (mg/ml) T 24 h 5° C. |
|---|---|---|---|---|---|
| 2 | DMI/water 1:1 | Hydrochloric | 290 | 250 | 280 |
| 3 | DMI/water 1:1 | Methanesulfonic | 280 | 280 | 300 |

TABLE 3-continued

Solubility of rifabutin reconstituted solutions at t = 0 and t = 24 h

| Example No. | Solvent/water mix | Acid | Solubility (mg/ml) T0 | Solubility (mg/ml) T 24 h RT | Solubility (mg/ml) T 24 h 5° C. |
|---|---|---|---|---|---|
| 4 | DMI/water 1:1 | Phosphoric | 300 | 210 | 190 |
| 5 | DMI/water 1:1 | L-Tartaric | 240 | 230 | 250 |
| 6 | DMI/water 1:1 | D-Glucuronic | 300 | 260 | 260 |
| 7 | DMI/water 1:1 | L-Malic | 300 | 200 | 210 |
| 8 | DMI/water 1:1 | D-Gluconic | 300 | 260 | 260 |
| 9 | DMI/water 1:1 | L-Lactic | 260 | 200 | 290 |
| 10 | DMI/water 1:1 | Acetic | 290 | 250 | 270 |
| 11 | DMI/water 1:1 | L-Aspartic | 40 | 40 | 40 |
| 17 | Transcutol/water 1:2 | D-glucuronic | 130 | 172 | — |
| 18 | Transcutol/water 1:2 | acetic | — | 130 | — |
| 19 | DMI/water 1:2 | D-glucuronic | 150 | 180 | — |
| 20 | DMI/water 1:2 | acetic | 160 | 150 | — |

TABLE 4

Solubility and pH at t = 0 and t = 24 h of reconstituted rifabutin solutions diluted with 0.9% saline

| Example No. | Solvent/water mix + Acid | Dilution in 0.9% saline | Solubility (mg/mL) T 0 | Solubility (mg/mL) T 24 h RT | pH T 0 h | pH T 24 h |
|---|---|---|---|---|---|---|
| 1 | DMI/water 1:1 + — | 10x | 2 | 2 | 7.1 | 6.6 |
| 2 | DMI/water 1:1 + Hydrochloric | 10x | 23 | 18 | 2.5 | 2.6 |
| 3 | DMI/water 1:1 + Methanesulfonic | 10x | 25 | 28 | 2.5 | 2.6 |
| 4 | DMI/water 1:1 + Phosphoric | 10x | 20 | 24 | 2.5 | 2.6 |
| 5 | DMI/water 1:1 + L-Tartaric | 10x | 23 | 23 | 3.2 | 3.2 |
| 6 | DMI/water 1:1 + D-Glucuronic | 10x | 26 | 28 | 3.8 | 4.0 |
| 7 | DMI/water 1:1 + L-Malic | 10x | 19 | 22 | 3.6 | 3.6 |
| 8 | DMI/water 1:1 + D-Gluconic | 10x | 16 | 25 | 5.8 | 4.3 |
| 9 | DMI/water 1:1 + L-Lactic | 10x | 20 | 25 | 4.1 | 4.2 |
| 10 | DMI/water 1:1 + Acetic | 10x | 26 | 25 | 5.1 | 5.2 |
| 11 | DMI/water 1:1 + L-Aspartic | 10x | 3 | 3 | 6.3 | 6.1 |
| 17 | Transcutol/water 1:2 + D-glucuronic | 6.67x | 22 | 23 | — | — |
| 18 | Transcutol/water 1:2 + acetic | 6.67x | 21 | 22 | — | — |
| 19 | DMI/water 1:2 + D-glucuronic | 6.67x | 22 | 24 | — | — |
| 20 | DMI/water 1:2 + acetic | 6.67x | 19 | 18 | — | — |
| 1 | DMI/water 1:1 + — | 100x | 0.3 | 0.4 | 7.2 | 7.3 |
| 2 | DMI/water 1:1 + Hydrochloric | 100x | 2.5 | 2.5 | 4.2 | 3.9 |
| 3 | DMI/water 1:1 + Methanesulfonic | 100x | 2.6 | 2.6 | 4.1 | 3.8 |
| 4 | DMI/water 1:1 + Phosphoric | 100x | 2.3 | 2.2 | 3.5 | 3.3 |
| 5 | DMI/water 1:1 + L-Tartaric | 100x | 2.3 | 2.2 | 3.4 | 3.4 |
| 6 | DMI/water 1:1 + D-Glucuronic | 100x | 2.5 | 2.3 | 4.8 | 4.2 |
| 7 | DMI/water 1:1 + L-Malic | 100x | 1.9 | 1.9 | 3.9 | 3.7 |
| 8 | DMI/water 1:1 + D-Gluconic | 100x | 2.2 | 1.9 | 5.9 | 4.4 |
| 9 | DMI/water 1:1 + L-Lactic | 100x | 2.5 | 2.4 | 4.5 | 4.3 |
| 10 | DMI/water 1:1 + Acetic | 100x | 2.5 | 2.3 | 5.2 | 5.2 |
| 11 | DMI/water 1:1 + L-Aspartic | 100x | 0.4 | 0.4 | 6.6 | 6.5 |

Example 3

Large scale evaluation for reconstitution of rifabutin and further dilution with 0.9% saline: 1.50 g (1.77 mmoles) of rifabutin powder were weighed into a 40 mL glass vial. An equimolar amount of acid (1.77 mmoles) dissolved in 6 mL dimethyl isosorbide/water 50/50 (v/v) was added. The solutions were vortexed for 30 seconds, vigorously stirred at RT for 15 minutes using a magnetic stirring bar and again vortexed for 30 seconds.

The samples were filtrated, using a syringe and filter (0.2 μm PTFE filter), and the concentration of reconstituted rifabutin solution was determined by HPLC analysis. Aliquots (1 mL) of the undiluted solutions were stored at RT and at 5° C. for 24 hours.

Figure 2:
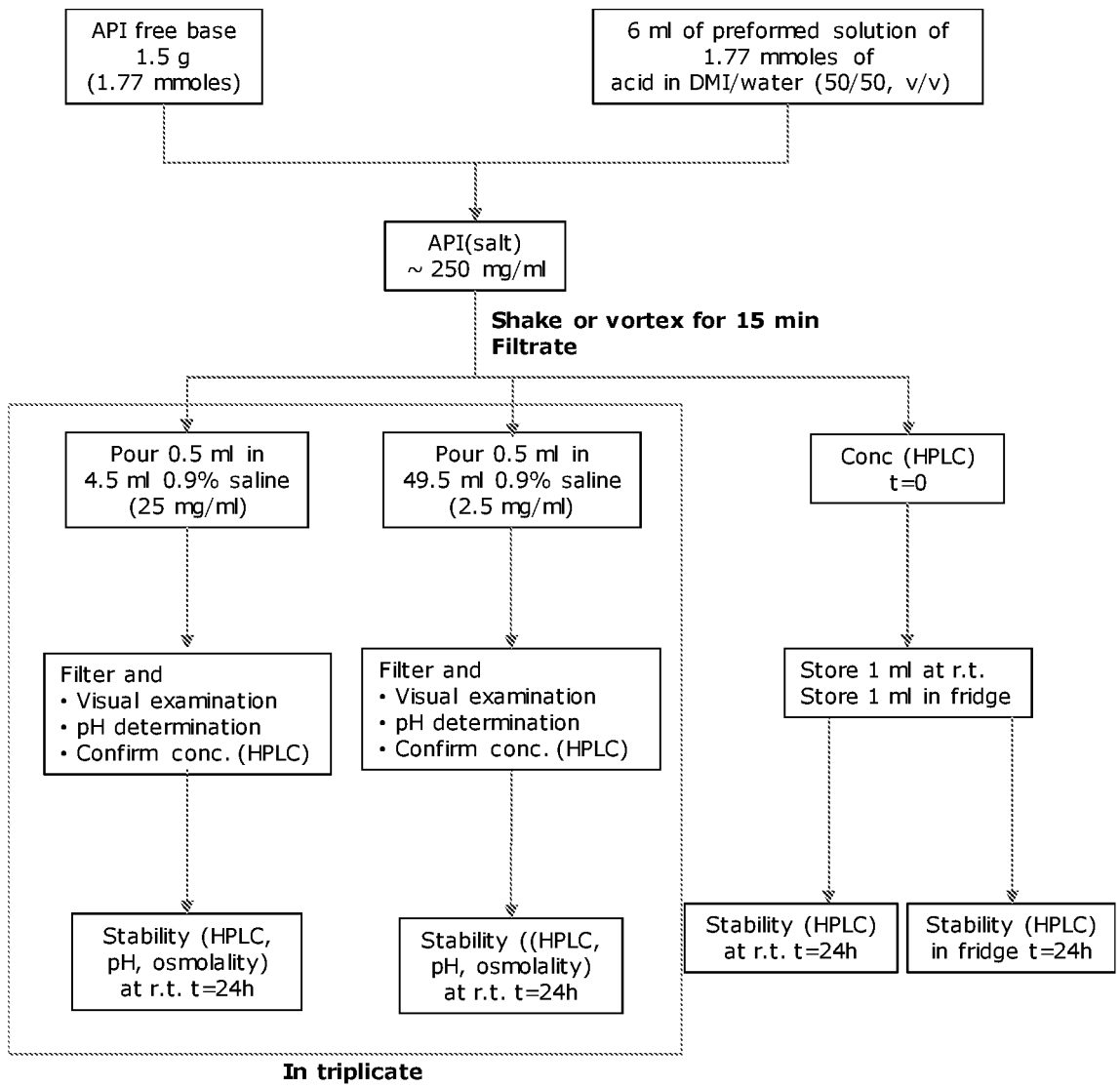
FIG. 2 is a schematic illustration of methods of analysis of rifabutin formulations.

FIG. 2 is a schematic representation illustrating methods of analysis of rifabutin formulations. Aliquots (500 μL) of the filtrate were diluted 10-fold and 100-fold in 0.9% saline. These dilutions were prepared in triplicate. The diluted samples were visually inspected for immediate precipitation and were filtered after 15 min. The concentration of API was determined by HPLC analysis and the pH was recorded. The diluted samples were stored at RT for 24 hours.

After the storage time of 24 hours, the diluted and undiluted samples were reanalyzed by HPLC analysis for determination of the API concentration and the pH was recorded.

Figure 3:
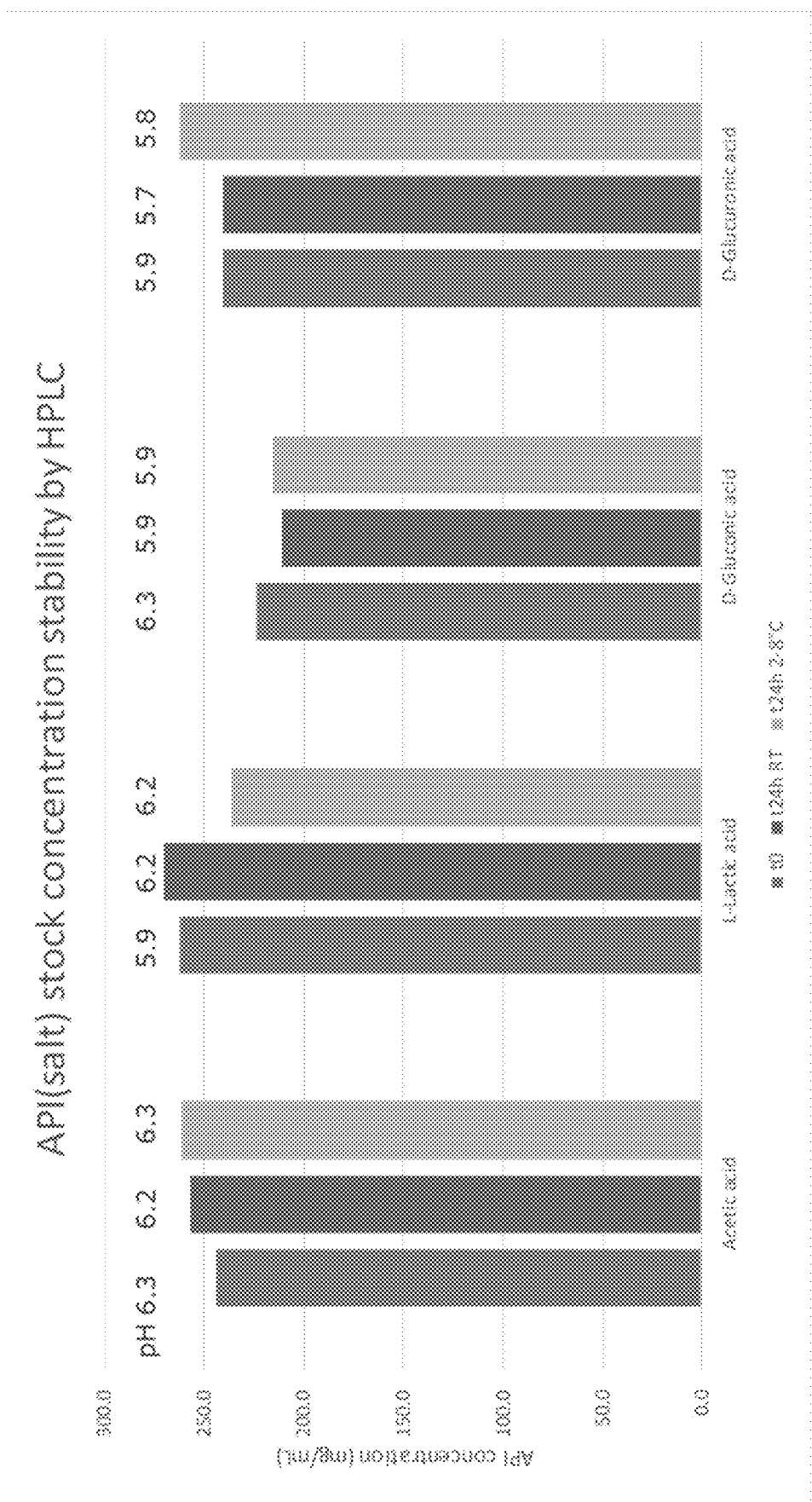
FIG. 3 is a graph showing rifabutin solubility in formulations.
Figure 4:
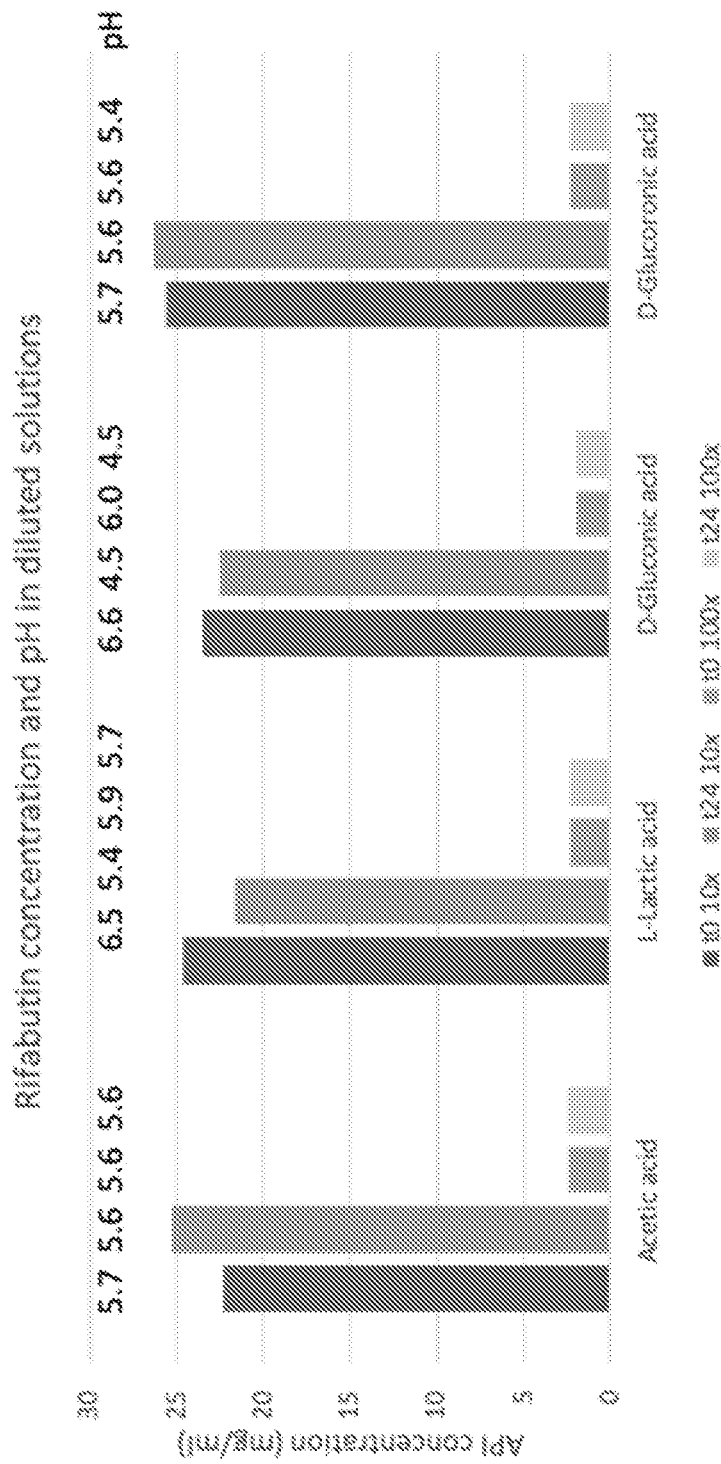
FIG. 4 is a graph showing rifabutin solubility in formulations.

The experimental details, results and recorded pH values of the solubility tests of the undiluted samples are shown in Tables 5, 6 and 7 and graphically represented in FIGS. 3 and 4.

TABLE 5

Concentration and pH of reconstituted rifabutin solutions at t = 0 and stored for 24 hours at 5° C. and room temperature

| Acid | Time = 0 Concentration mg/ml | pH | Time = 24 hours Room temperature Concentration mg/ml | pH | Time = 24 hours 5° C. Concentration mg/ml | pH |
|---|---|---|---|---|---|---|
| Acetic acid | 244 | 6.3 | 257 | 6.2 | 262 | 6.3 |
| L-Lactic acid | 263 | 5.9 | 270 | 6.2 | 236 | 6.2 |
| D-Gluconic acid | 224 | 6.3 | 211 | 5.9 | 216 | 5.9 |
| D-Glucuronic acid | 241 | 5.9 | 241 | 5.7 | 262 | 5.8 |

FIG. 3 is a graph showing rifabutin solubility in formulations. Undiluted samples at 5 larger scale were analyzed at to (blue bars), after 24 hours at room temperature (red bars), and after 24 hours at 5° C. (green bars).

TABLE 6

Concentration and pH of rifabutin solutions at a nominal concentration of 25 mg/ml stored for 24 hours at room temperature*.

| Acid | reconstituted solution Concentration mg/ml | pH | 10 fold dilution Time = 0 Concentration mg/ml | pH | 10 fold dilution Time = 24 hours Concentration mg/ml | pH |
|---|---|---|---|---|---|---|
| Acetic acid | 244 | 6.3 | 22.3 ± 3.4 | 5.7 | 25.3 ± 2.4 | 5.6 |
| L-Lactic acid | 263 | 5.9 | 24.6 ± 1.2 | 6.5 | 21.6 ± 0.7 | 5.4 |
| D-Gluconic acid | 224 | 6.3 | 23.5 ± 1.0 | 6.6 | 22.5 ± 1.6 | 4.5 |
| D-Glucuronic acid | 241 | 5.9 | 25.6 ± 0.6 | 5.7 | 26.3 ± 1.2 | 5.6 |

*The experiment has been performed in triplicate.

Osmolality of these solutions was 632, 644, 622 and 645 mOsm/kg, respectively for the solutions generated from acetic acid, L-lactic acid, D-gluconic acid and D-glucuronic acid.

TABLE 7

Concentration and pH of rifabutin solutions at a nominal concentration of 2.5 mg/ml stored for 24 hours at room temperature*.

| Acid | reconstituted solution Concentration mg/ml | pH | 100 fold dilution Time = 0 Concentration mg/ml | pH | 100 fold dilution Time = 24 hours Concentration mg/ml | pH |
|---|---|---|---|---|---|---|
| Acetic acid | 244 | 6.3 | 2.4 ± 0.0 | 5.6 | 2.4 ± 0.0 | 5.6 |
| L-Lactic acid | 263 | 5.9 | 2.3 ± 0.0 | 5.9 | 2.2 ± 0.0 | 5.7 |
| D-Gluconic acid | 224 | 6.3 | 2.0 ± 0.0 | 6.0 | 2.0 ± 0.0 | 4.5 |
| D-Glucuronic acid | 241 | 5.9 | 2.3 ± 0.0 | 5.6 | 2.3 ± 0.0 | 5.4 |

*The experiment has been performed in triplicate.

Osmolality of these solutions was 323, 319, 316 and 318 mOsm/kg, respectively for the solutions generated from acetic acid, L-lactic acid, D-gluconic acid and D-glucuronic acid.

FIG. 4 is a graph showing rifabutin solubility in formulations.

Diluted samples were analyzed at to (blue bars, 10× dilution; grey bars 100× dilution) and after 24 hours at room temperature (orange bars, 10× dilution; yellow bars 100× dilution).

Example 4

Reconstitution of rifabutin from a solution of rifabutin in transcutol HP and further dilution with 0.9% saline: 1.50 g (1.77 mmoles) of rifabutin powder were weighed into a 40 mL glass vial. 3 ml of DMI or 3 ml of transcutol HP were added and the very thick suspension was swirled for about 6 and 18 hours, respectively in order to obtain a very dense solution. The solutions were filtered sterile through a 0.2 μm filter (PTFE filter). To an aliquot of 1 ml of the two solutions containing about 500 mg (about 0.590 mmols) of rifabutin, 1 ml of a solution of water containing 0.590 mmols of acetic acid was added under gentle swirling. A perfect solution formed extemporarily. Analysis pre and post filtration (0.2 µm PTFE filter) show a similar titer for all solutions in agreement with the results reported in Example 3.

To another aliquot of 1 ml of the two solutions containing about 500 mg (about 0.590 mmols) of rifabutin, 5 ml of a solution of water/0.9% saline 1:4 containing 0.590 mmols of acetic acid were added. A perfect solution formed extemporarily. Analysis pre and post filtration (0.2 µm PTFE filter) show a similar titer of all solutions from about 46.7 to 48.2 mg/ml.

Example 5

Analytical methods and sample preparation for the determination of the solubility: Dilutions for the solubility determination were prepared by adding 25 µL of the mother liquor to 500 µL of 0.1% TFA in acetonitrile (dilution 1 21-fold). If necessary, a second dilution was prepared by adding 25 µL of dilution 1 to 500 µL of 0.1% TFA in acetonitrile (441-fold dilution).
LCMS Method
HPLC: Agilent 1200
Detector 1: DAD set at 276 nm
Detector 2: Mass Spectrometer
HPLC Conditions:
Column: Sunfire C18 (100×4.6 mm×3.5 µm)
Column temp: 35° C.
Flow cell: 10 mm path
Mobile phase A: 0.1% TFA in Water
Mobile phase B: 0.1% TFA in Acetonitrile
Flow: 1.0 ml/min

| HPLC mobile phase gradient. Time (min) | Mobile phase A (%) | Mobile phase B (%) |
| --- | --- | --- |
| 0 | 90 | 10 |
| 9 | 10 | 90 |
| 10 | 90 | 10 |
| 11 | 90 | 10 |

Rifabutin had a retention time of 6.8-6.9 min. The peak area observed from the UV detector of the compound of interest was employed for the calculation of concentration of the component in the solution. It was verified that there was no interference with the ingredients of the vehicles.

Table 3 and Table 5 report the concentration of rifabutin in solutions containing 1 molar equivalent of an acid in dimethyl isosorbide/water 50/50 (v/v) or transcutol HP/water 33.3/66.7 (v/v) freshly prepared and after storage at room temperature (RT) or 5° C. for 24 hours.

Reconstituted solutions can be stored for 24 hours at RT and at 5° C.

Table 4, Table 6 and Table 7 report the concentration of rifabutin after up to 100-fold dilution in 0.9% saline and storage at RT for 24 hours. The pH and osmolity of the solutions was also recorded.

Reconstituted solutions may be diluted without restriction in order to render a composition suitable for a desired route of administration.

Dilution of reconstituted solutions with 0.9% saline has a final pH that depends on the pKa of the acid used, and a preferred acid should have a pKa value greater than 2, preferably greater than 3. Preferably such acids are D-glucuronic acid, D-gluconic acid, L-lactic acid and acetic acid. Most preferably the acid is acetic acid or D-glucuronic acid.

Example 6

Reconstitution of Rifabutin from a Large Scale Solution of Rifabutin in DMI and Further Dilution with 0.9% Saline:

Preparation of vial 1: 1200 ml of DMI was heated at 40° C. in a 5 L glass tank and 600 g (0.708 moles) of rifabutin powder is added portion-wise under stirring at 40° C. Complete dissolution was obtained in about 6 hours and the solution was allowed to return to room temperature. The solution was then filtered through a PVDF (polyvinylidene fluoride), Nylon, or PTFE (polytetrafluoroethylene) 0.22 µm sterile filter. A volume of solution equivalent to 500 mg (0.590 mmoles) of rifabutin was transferred into 10 ml sterile and depyrogenized vials via sterile tubing and the vials were sealed with Fluorotec rubber stoppers and flip-off overseals. Additionally or alternatively, the vials underwent terminal sterilization at 121° C. for 20 minutes in an autoclave. This procedure was repeated starting from two different rifabutin batches.

Analysis and stability data after terminal sterilization are reported in Tables 8 and 9, respectively.

Preparation of vial 2: a solution of 4% w/v acetic acid in sterile water for injection was transferred into 10 ml sterile and depyrogenized vials via sterile tubing and the vials were sealed with Fluorotec rubber stoppers and flip-off overseals and underwent terminal sterilization in an autoclave.

Reconstitution of rifabutin before use: 1 ml of sterile 4% w/v acetic acid (0.66 mmoles) in water for injection was withdrawn by means of 1 ml syringe from vial 2 and was added to vial 1 under gentle swirling.

Dilution of reconstituted rifabutin solution in 0.9% saline: The reconstituted solution was brought to a total volume of 10 ml by addition of sterile solution of 0.9% NaCl solution (saline for injection) to bring final concentration of rifabutin to 50 mg/ml.

Analysis data are reported in Table 10

Alternatively, the reconstituted solution can be withdrawn from the vial by means of a syringe and directly injected into a saline bag for infusion.

TABLE 8

Analysis of vial 1 prepared from two different rifabutin batches

| | | Compliance and results | |
| --- | --- | --- | --- |
| Test | | From API batch 1 | From API batch 2 |
| Appearance (vial crimped and sealed) | | comply | comply |
| Color and clarity (reddish-violet dense solution, free of visible particles) | | comply | comply |
| Vial content in mg/ml (500 mg ± 10%) | | 507.6 | 492.2 |
| Related substances | Impurity E | 0.0 * | 0.0 * |
| | Impurity B | −0.1 * | 0.1 * |
| | Impurity D | 0.0 * | 0.0 * |
| | Impurity C | 0.0 * | −0.1 * |
| | RRT1.6-1.7 | −0.05; −0.1 * | 0.0 * |
| | Any other impurity | 0.3 * | 0.0 * |
| | Total of all impurities | 1.1 * | 0.1 * |

*Variation in impurity content of rifabutin in vial 1 from rifabutin drug substance (API). Data are impurity % and are reported as % impurity in vial 1-% impurity in API.

TABLE 9

Stability results of vial 1 stored at 2-8° C. and at 25° C. ± 2° C./60% RH ± 5% RH

|  | Test | Stability results * Vial 1 stored at 2-8° C. | | | Stability results * Vial 1 stored at 25° C./60% RH | | |
| --- | --- | --- | --- | --- | --- | --- | --- |
|  |  | T = 15 days | T = 30 days | T = 90 days | T = 15 days | T = 30 days | T = 90 days |
| Related | Impurity E | 0.1 | 0.1 | 0.0 | 0.1 | 0.1 | 0.0 |
| substances | Impurity B | −0.2 | −0.2 | −0.2 | −0.2 | −0.2 | −0.2 |
|  | Impurity D | 0.0 | 0.0 | 0.0 | 0.0 | 0.0 | 0.0 |
|  | Impurity C | 0.0 | 0.0 | 0.0 | 0.0 | 0.0 | 0.0 |
|  | RRT1.6-1.7 | 0.0 | 0.0 | 0.05; 0.1 | 0.0 | 0.0 | 0.25; 0.3 |
|  | Any other impurity | 0.1 | 0.0 | 0.0 | 0.1 | 0.1 | −0.1 |
|  | Total of all impurities | 0.3 | 0.3 | −0.1 | 0.4 | 0.4 | −0.1 |

* Variation in impurity content of rifabutin in vial 1 upon storage at different conditions. Data are impurity % and are reported as % impurity in vial 1 at day 15, 30 and 90 - % impurity in vial 1 at day 0.

TABLE 10

Analysis of reconstituted solutions after dilution to 50 mg/ml 0.9% saline

| Test | Compliance and results |
| --- | --- |
| Color and clarity (reddish-violet dense solution, free of visible particles) | comply |
| Rifabutin concentration in mg/ml (50 mg/ml ± 10%) | 51.7 |
| pH | 5.6 |
| Related substances   Impurity E |  |
| Impurity B | −0.1 * |
| Impurity D | 0.0 * |
| Impurity C | −0.05 * |
| RRT1.6-1.7 | 0.15; 0.2 * |
| Any other impurity | −0.3 * |
| Total of all impurities | −0.6 * |

* Variation in impurity content of rifabutin after reconstitution and dilution with 0.9% saline Data are impurity % and are reported as % impurity in reconstituted/diluted solution-% impurity in vial 1.

Example 7

Analytical Methods and Sample Preparation for Stability Studies and Impurity Determination
HPLC Conditions

| HPLC Apparatus | HPLC Waters Alliance equipped with UV detector or equivalent |
| --- | --- |
| Software | Empower 3 System or equivalent |
| Column | C8, 5 μm, 4.5 × 150 mm, Waters Spherisorb |
| Flow rate | 1.0 ml/min |
| Injection volume | 10 μl |
| Wavelength | 254 nm |
| Mobile phase | 55% ACN + 45% of 13.6 g/L (0.1M) of potassium dihydrogen phosphate. The mixture has to be adjusted to pH6.5 ± 0.1 with 2N NaOH |
| Elution | Isocratic |
| Run time | 2.5 times the retention time of rifabutin |
| RRT (with reference to Rifabutin) | Rifabutin: 1 (about 9 min) Imp. E: about 0.5 Imp. B: about 0.6 Imp. D: about 0.8 Imp. C: about 1.4 |

Sample Preparation
Blank solution: mobile phase as it is.
Test Solution 1—for Determination of the Concentration of the Rifabutin in a Bulk Solution:
0.5 mg of Rifabutin was transferred to a solution in DMI, accurately weighed, to a 10-mL volumetric flask and diluted to volume with acetonitrile. 1.5 ml of the obtained solution was transferred into a 50 ml-volumetric flask, dilute with mobile phase to volume, and mixed (0.5 mg/ml).
Test Solution 2—for the Vial Content Determination:
After removal of the vial flip-off, about 5 ml of ACN in the sealed vial was transferred by using a 10 ml syringe. The obtained solution was then transferred into a 50 ml volumetric flask and washed at least 5 times with ACN by adding the washing solution into the 50 ml volumetric flask, in order to obtain an accurate recovery of the whole amount of solution of the vial. The seal and the stopper was then removed and another two washes of the vial were performed. The volume was then diluted with ACN.
Lastly the obtained solution was diluted 1 ml to 20 ml with the mobile phase and mix (0.5 mg/ml).
Standard solution: about 25 mg of Rifabutin CRS, accurately weighed, was transferred to a 50-mL volumetric flask. 5 mL of acetonitrile was added and the solution was diluted with mobile phase to volume, and mixed (0.5 mg/ml).
Diluted Standard solution: 1 ml of Rifabutin standard solution was diluted to 100 ml with mobile phase (0.005 mg/ml).
Resolution solution: about 10 mg of Rifabutin CRS was dissolved in 2 ml MeOH, 1 ml of 2N NaOH was added and the solution allowed to stand for about 4 min. 1 ml of 2N HCl was added and the solution diluted to 50 ml with the mobile phase.
System Suitability
  On the Resolution solution: the chromatogram exhibited a major peak for a degradant, two minor peaks for degradants, and a major peak for Rifabutin at RRT of about 0.5, 0.6, 0.8, and 1.0, respectively. The resolution between the Rifabutin peak and the degradant peak eluting at a relative retention time of about 0.8 was not less than 1.3.
  On the Standard preparation: the column efficiency was not less than 2000 theoretical plates, and the relative standard deviation for replicate injections was not more than 2.0%.
Calculations for Test Solution 1
Calculation of the quantity, in mg, of Rifabutin in each g of sample is performed using the formula:

$$\text{mg Rifabutin} = \left(\frac{C \times P}{W}\right) \times \left(\frac{AT}{AS}\right) \times \frac{50 \times 10}{1.5}$$

in which
C=standard concentration (mg/mL)
P=standard potency (µg/mg),
W=sample weight (g)
AT=area of sample peak
AS=average area of standard peak
Calculation of the percentage of each impurity is performed using the formula:

$$\% \text{ each impurity} = \left(\frac{C \times P}{W}\right) \times \left(\frac{AI}{AS}\right) \times \frac{50 \times 10}{1.5 \times R}$$

in which
C=diluted standard concentration (mg/mL)
P=standard potency (µg/mg)
W=sample weight (g)
AI=area of impurity peak
AS=area of standard peak
R=mg Rifabutin in each g of sample calculated concentration (mg/g)

Calculations for Test Solution 2
Calculation of the content of Rifabutin, in g, in each vial is performed using the formula:

$$\text{mg Rifabutin per vial} = (C \times P) \times \left(\frac{AT}{AS}\right) \times \frac{50 \times 20}{1}$$

in which
C=standard concentration (mg/mL)
P=standard potency (µg/mg),
W=sample weight (g)
AT=area of sample peak
AS=average area of standard peak
Calculation of the percentage of each impurity is performed using the formula:

$$\% \text{ each impurity} = (C \times P) \times \left(\frac{AI}{AS}\right) \times \frac{50 \times 20}{1 \times R}$$

in which
C=diluted standard concentration (mg/mL)
P=standard potency (µg/mg)
W=sample weight (g)
AI=area of impurity peak
AS=area of standard peak
R=mg Rifabutin in each vial

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

What is claimed is:

1. A rifabutin formulation comprising:
    a solution comprising a solvent, water, an acid, and rifabutin in aqueous solution at a concentration between about 50 mg/mL and about 250 mg/mL.

2. The formulation of claim 1, wherein the solvent is selected from the group consisting of polyoxyethylene sorbitan monooleate, polyoxyethylene sorbitan monolaurate, polyethylene glycol (PEG), propylene glycol, N-methyl-2-pyrrolidone (NMP), glycerin, ethanol, dimethylacetamide (DMA), diethylene glycol monoethyl ether (transcutol HP), and dimethyl isosorbide (DMI).

3. The formulation of claim 1, wherein the solvent is polyoxyethylene sorbitan monooleate or polyoxyethylene sorbitan monolaurate.

4. The formulation of claim 1, wherein the acid is selected from a group consisting of hydrochloric acid, methanesulfonic acid, phosphoric acid, L-tartaric acid, D-glucuronic acid, L-malic acid, D-gluconic acid, L-lactic acid, acetic acid, and L-aspartic acid.

5. The formulation of claim 1, wherein the acid is acetic acid or D-glucuronic acid.

6. The formulation of claim 1, wherein the solution is contained within an IV bag.

7. The formulation of claim 1, wherein the formulation is an inhalable formulation.

8. The formulation of claim 1, wherein the rifabutin is present as a free base.

9. The formulation of claim 1, wherein the rifabutin is present as a pharmaceutically acceptable salt.

10. The formulation of claim 9, wherein the pharmaceutically acceptable salt is an acid addition salt formed with an acid selected from the group consisting of hydrochloric acid, hydrobromic acid, phosphoric acid, sulfuric acid, perchloric acid, acetic acid, maleic acid, tartaric acid, citric acid, succinic acid, methanesulfonic acid, glucuronic acid, malic acid, gluconic acid, lactic acid, aspartic acid, and malonic acid.

* * * * *